United States Patent
Williams et al.

[11] Patent Number: 5,872,250
[45] Date of Patent: Feb. 16, 1999

[54] PROCESS FOR SYNTHESIZING CARBAPENEM ANTIBIOTICS

[75] Inventors: John M. Williams, Belle Mead; Ronald B. Jobson, East Brunswick, both of N.J.

[73] Assignee: Merck & Co., Inc., Rahway, N.J.

[21] Appl. No.: 887,849

[22] Filed: Jul. 30, 1997

[51] Int. Cl.$^6$ .................. C07D 477/20; C07D 207/16
[52] U.S. Cl. ............................. 540/350; 548/556
[58] Field of Search ............................. 540/350

[56] References Cited

FOREIGN PATENT DOCUMENTS

WO 93/15078 8/1993 WIPO .

OTHER PUBLICATIONS

M. Sunagawa et al., J. Antibiotic, 44(4) pp. 459–462, 1991.
M. Sunagawa et al., J. Antibiotic, 43(5) pp. 519–532, 1990.

Primary Examiner—Mark L. Berch
Attorney, Agent, or Firm—Sylvia A. Ayler; Richard C. Billups; Mark R. Daniel

[57] ABSTRACT

A process for synthesizing a compound of the formula I:

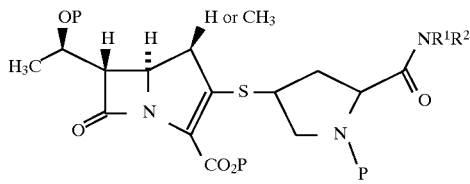

or a pharmaceutically acceptable salt or ester thereof, wherein each P independently represents H or a protecting group, and $R^1$ and $R^2$ independently represent H, $C_{1-10}$ alkyl, aryl or heteroaryl, or substituted $C_{1-10}$ alkyl, aryl or heteroaryl, comprising:

reacting the compounds:

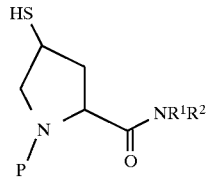

or a pharmaceutically acceptable salt or ester thereof, and

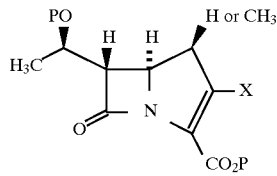

or a pharmaceutically acceptable salt or ester thereof, wherein X represents $OP(O)(OR)_2$, or $OSO_2R$, wherein R represents $C_{1-6}$ alkyl, aryl or perfluoro $C_{1-6}$ alkyl, in the presence of an amine selected from the group consisting of: diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0]undec-7-ene (DBU) and 1,5-diazabicyclo[4.3.0]non-5-ene to produce a compound of formula I.

5 Claims, No Drawings

PROCESS FOR SYNTHESIZING CARBAPENEM ANTIBIOTICS

BACKGROUND OF THE INVENTION

The present invention relates to the synthesis of carbapenem antibiotics. It has been discovered that the inclusion of a secondary amine in the coupling reactions described herein significantly and surprisingly enhances the rate of reaction, allowing for shorter reaction times and relatively complete conversion at lower temperatures than observed when tertiary amines are used in this type of reaction.

Triethyl and diisopropylethyl amines have been reported to be useful in these reactions, but the reaction times and conditions have been unacceptable from a commercial standpoint. For example, WO 93/15078 published on Aug. 5, 1993, relates to similar reactions in the presence of a tertiary amine, such as diisopropyl-ethylamine, or an inorganic base, such as an alkali metal carbonate, e.g., potassium carbonate. Such reactions are performed at a temperature between −25° C. and ambient temperature.

One object of the present invention is to effect a reaction between the carbapenem base molecule and the 2-position side chain which is sufficiently rapid and efficient to minimize the formation of side reaction products, and to avoid the need for inappropriate high and low temperatures and other reaction conditions.

Another object of the present invention is to avoid the use of catalysts and other reaction components which would require a separate removal step if traces thereof were contained in the final product.

These and other objects will be apparent from the teachings contained herein.

SUMMARY OF THE INVENTION

A process for synthesizing a compound of the formula I:

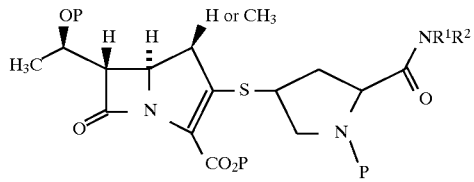

or a pharmaceutically acceptable salt or ester thereof, is disclosed, wherein each P independently represents H or a protecting group, and $R^1$ and $R^2$ independently represent H, $C_{1-10}$ alkyl, aryl or heteroaryl, or substituted $C_{1-10}$ alkyl, aryl or heteroaryl, comprising:
reacting the compounds:

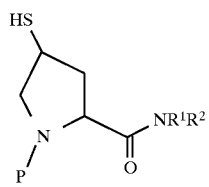

or a pharmaceutically acceptable salt or ester thereof, and

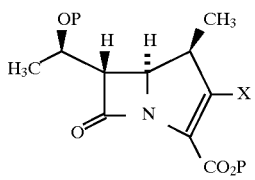

or a pharmaceutically acceptable salt or ester thereof, wherein X represents $OP(O)(OR)_2$, or $OSO_2R$, wherein R represents $C_{1-6}$ alkyl, $C_{1-6}$ alkaryl, aryl or perfluoro $C_{1-6}$ alkyl, in the presence of an amine selected from the group consisting of:
diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0]undec-7-ene (DBU) and 1,5-diazabicyclo[4.3.0]non-5-ene (DBN)
to produce a compound of formula I.

DETAILED DESCRIPTION OF THE INVENTION

It has been discovered that the amines described herein facilitate a reaction between compounds of formulas II and III. With respect to compounds of formulas II and III, these compounds can be made in accordance with techniques such as those which are disclosed in U.S. Pat. Nos. 5,034,384 granted on Jul. 23, 1991, and 4,994,568 granted on Feb. 19, 1991, incorporated herein by reference.

Compounds such as compound IIa and IIIa, can likewise be produced in accordance with U.S. Pat. No. 5,478,820 granted on Dec. 26, 1995, incorporated herein by reference.

The reactions described herein are preferably run in a polar aprotic solvent. Preferred examples of polar aprotic solvents include dimethylformamide, N-ethylpyrrolidinone and acetonitrile.

In a preferred aspect of the invention a process for synthesizing a compound of the formula Ia:

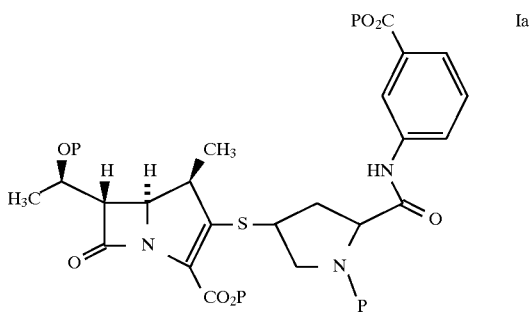

or a pharmaceutically acceptable salt or ester thereof, is described herein wherein each P independently represents H or a protecting group, comprising:
reacting the compounds:

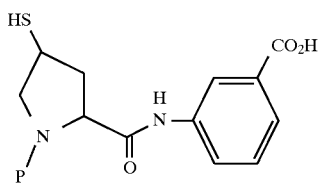

or a pharmaceutically acceptable salt or ester thereof, and

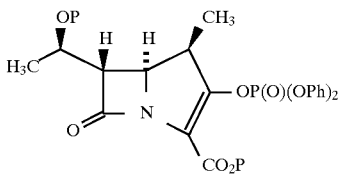

or a pharmaceutically acceptable salt or ester thereof, wherein Ph represents phenyl, in the presence of an amine selected from the group consisting of:
diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0]undec-7-ene (DBU) and 1,5-diazabicyclo [4.3.0]non-5-ene (DBN)
to produce a compound of formula Ia.

The invention is described herein in detail using the terms defined below unless otherwise specified.

The term "alkyl" refers to a monovalent alkane (hydrocarbon) derived radical containing from 1 to 15 carbon atoms unless otherwise defined. It may be straight or branched, and when of sufficient size, e.g., $C_{3-15}$ may be cyclic. Preferred straight or branched alkyl groups include methyl, ethyl, propyl, isopropyl, butyl and t-butyl. Preferred cycloalkyl groups include cyclopropyl, cyclopentyl and cyclohexyl.

Alkyl also includes an alkyl group substituted with a cycloalkyl group, such as cyclopropylmethyl.

When substituted alkyl is present, this refers to a straight, branched or cyclic alkyl group as defined above, substituted with 1–3 groups as defined with respect to each variable.

Heteroalkyl means an alkyl group containing from 2–15 carbon atoms and being interrupted by from 1–4 heteroatoms selected from O, S and N.

The term "alkenyl" refers to a hydrocarbon radical straight, branched or cyclic containing from 2 to 15 carbon atoms and at least one carbon to carbon double bond. Preferably one carbon to carbon double bond is present, and up to four non-aromatic (non-resonating) carbon-carbon double bonds may be present. Preferred alkenyl groups include ethenyl, propenyl, butenyl and cyclohexenyl. As described above with respect to alkyl, the straight, branched or cyclic portion of the alkenyl group may contain double bonds and may be substituted when a substituted alkenyl group is provided.

The term "alkynyl" refers to a hydrocarbon radical straight, branched or cyclic, containing from 2 to 15 carbon atoms and at least one carbon to carbon triple bond. Up to three carbon-carbon triple bonds may be present. Preferred alkynyl groups include ethynyl, propynyl and butynyl. As described above with respect to alkyl, the straight, branched or cyclic portion of the alkynyl group may contain triple bonds and may be substituted when a substituted alkynyl group is provided.

Aryl refers to aromatic rings e.g., phenyl, substituted phenyl and like groups as well as rings which are fused, e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted as defined below. Preferred substituted aryls include phenyl and naphthyl substituted with one to three groups, such as selected from halo, alkyl and trifluoromethyl.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. The heteroaryl group is optionally substituted with up to three groups.

Heteroaryl includes aromatic and partially aromatic groups which contain one or more heteroatoms. Examples of this type are thiophene, purine, imidazopyridine, pyridine, oxazole, thiazole, oxazine, pyrazole, tetrazole, imidazole, pyridine, pyrimidine, pyrazine and triazine. Examples of partially aromatic groups are tetrahydroimidazo[4,5-c]pyridine, phthalidyl and saccharinyl, as defined below.

Substituted alkyl, aryl and heteroaryl, and the substituted portions of aralkyl, aralkoxy, heteroaralkyl, heteroaralkoxy and like groups are substituted with from 1–3 groups selected from the group consisting of: halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, amino, alkylamino, dialkylamino, carboxy and sulfonylamino.

The terms "heterocycloalkyl" and "heterocyclyl" refer to a cycloalkyl group (nonaromatic) in which one of the carbon atoms in the ring is replaced by a heteroatom selected from O, S(O)y or N, and in which up to three additional carbon atoms may be replaced by said heteroatoms. When three heteroatoms are present in the heterocycle, they are not all linked together.

Examples of heterocyclyls are piperidinyl, morpholinyl, azetidinyl, pyrrolidinyl, tetrahydrofuranyl, imidazolinyl, piperazinyl, pyrolidin-2-one, piperidin-2-one and the like.

Acyl as used herein refers to —$C(O)C_{1-6}$ alkyl and —C(O)-aryl.

Acylamino refers to the group —$NHC(O)C_{1-6}$ alkyl and —NHC(O)aryl.

Aralkoxy refers to the group —$OC_{1-6}$ alkylaryl.

Alkaryl refers to $C_{1-6}$ alkyl-aryl-.

Alkylsulfonyl refers to the group —$SO_2C_{1-6}$ alkyl.

Alkylsulfonylamino refers to the group —$NHSO_2C_{1-6}$alkyl.

Arylsulfonylamino refers to the group —$NHSO_2$aryl.

Alkylaminocarbonyl refers to the group —$C(O)NHC_{1-6}$ alkyl.

Aryloxy refers to the group —O-aryl.

Sulfonylamino refers to the group —$NHSO_3H$.

Halo means Cl, F, Br and I selected on an independent basis.

The compounds of the present invention are useful in various pharmaceutically acceptable salt forms. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity and flowability of the resulting bulk drug. Conveniently, pharmaceutical compositions may be prepared from the active ingredients in combination with pharmaceutically acceptable carriers.

The pharmaceutically acceptable salts of the compounds of formula I include conventional non-toxic salts and quarternary ammonium salts of the compounds of formula I formed, e.g., with inorganic or organic cationic groups. For example, these salts include charge balancing cations which are present in association with the compound as necessary to maintain overall charge neutrality. Typically the charged specie would be a pharmaceutically acceptable salt-forming ion, such as sodium, potassium, magnesium and the like. When the counterion includes a bis cationic specie, e.g., $Ca^{+2}$ an appropriate amount is typically present relative to the carbapenem moiety to provide overall charge neutrality. Thus, a half molar equivalent of $Ca^{+2}$ can be included to maintain overall charge neutrality. All such embodiments are included in the present invention.

Numerous salt-forming ions are recited in Berge, S. M., et al. J. Pharm. Sci. 66(1): 1–16 (1977), the teachings of which are incorporated herein by reference.

A preferred group of salt-forming cations is selected from the group consisting of: sodium, potassium, calcium and magnesium.

More preferably the cation represents a member selected from the group consisting of: $Na^+$, $Ca^{+2}$ and $K^+$.

The pharmaceutically acceptable salts of the present invention can be synthesized by conventional chemical methods. Generally, the salts are prepared by reacting the free base or acid with stoichiometric amounts or with an excess of the desired salt-forming inorganic or organic acid or base, in a suitable solvent or solvent combination.

One preferred group of amines for use in the present invention includes diisopropylamine and dicyclohexylamine. These amines form crystalline salts with diphenylphosphoric acid, which crystallize from the coupling reaction mixture, affording an opportunity for removal of the phosphoric acid by-product of the reaction.

Using the amines noted above, the reaction rate is increased unexpectedly.

The compounds formed in the present invention have asymmetric centers and occur as racemates, racemic mixtures, and as individual diastereomers. The processes of synthesizing all such isomers, including optical isomers, are included in the present invention.

The carboxyl group at the 3-position and the hydroxyl group at the 8-position of the carbapenem, the pyrrolidinyl nitrogen and when present, the m-carboxyphenyl moiety may remain blocked until the final product is prepared. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable hydroxyl and carboxyl protecting groups are known in the art. See, e.g., T. W. Greene, *Protective Groups in Organic Synthesis,* John Wiley & Sons, Inc., 1981 (Chapters 2 and 5).

The invention is illustrated in connection with the following non-limiting examples.

PREPARATIVE EXAMPLE 1

(2S, 4S)-1-(ρ-Nitrobenzyloxycarbonyl)-2-(3-carboxyphenylcarbamoyl)-pyrrolidin-4-ylthiol:Sidechain thiol (B)

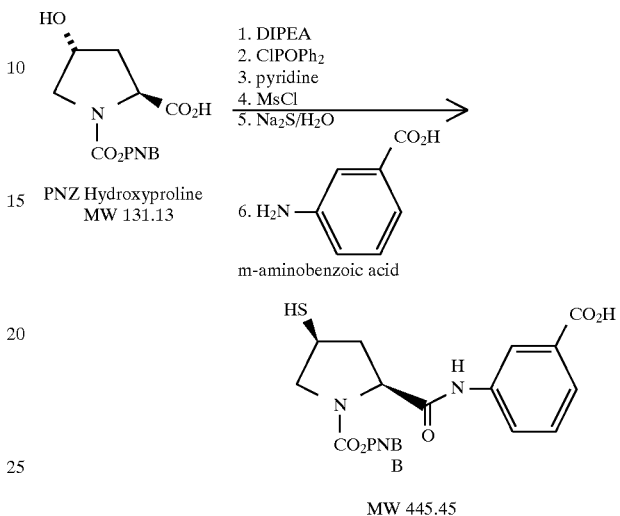

PNZ hydroxyproline (15 g) was stirred in a mixture of THF (225 mL) and toluene(75 mL), and the mixture was cooled to −10° C. Diisopropylethylamine (13.4 g) was added followed by a solution of 12.1 g of diphenylphosphinic chloride in 15 mL of toluene. The mixture was aged for 2 h at −10° C. and 4.1 g of pyridine in 4 mL of toluene was added followed by 6.29 g of methanesulfonyl chloride in 4 mL of toluene. After 4 h a solution of sodium sulfide trihydrate (7.0 g) in 75 mL of water was added and the mixture was warmed to 20° C. and aged for 14 h. The layers were separated and the organic layer was extracted with HCl (150 mL, 1.0 N), sodium bicarbonate (280 mL, 5%, 40°–45° C.), and aqueous NaCl (150 mL, saturated, 20°–25° C.).

To a 1 L flask was charged 540 mL of the extract, 6.6 g of m-aminobenzoic acid, and 1.0 mL of tributylphosphine. The mixture was degassed and was concentrated by atmospheric distillation to 200 mL. Toluene was added with continued distillation until the distillate temperature reached 110° C. Acetic acid (200 mL) and 1-propanol (200 mL) were added and the resulting mixture was cooled to 15°–20° C., and aged for 18 h. The product was isolated by filtration washing with 1-propanol and dried under vacuum at 80° C. to give 15.4 g of sidechain thiol.

Example 1

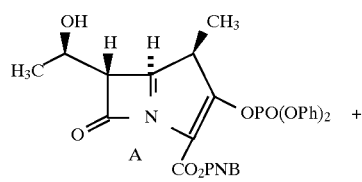

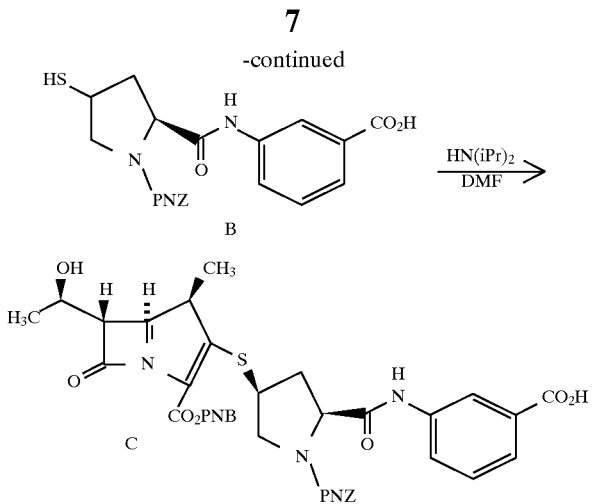

PNZ=p-nitrobenzyl carbamate
PNB=p-nitrobenzyl

Compound A (594 mg, 1.0 mmol) and compound B (454 mg, 1.02 mmol) were combined and DMF (2.0 mL) was added. The mixture was degassed. The resulting solution was cooled to −50 to −30° C. Diisopropylamine (204 mg, 0.28 mL) was added. The reaction was complete to >98% conversion in 2–3 hrs.

COMPARATIVE EXAMPLE

The procedure of Example One was followed, except that diisopropylamine was replaced with an equal molar quantity of diisopropylethylamine. The reaction was complete (98% conversion) after 18 h.

Example 2

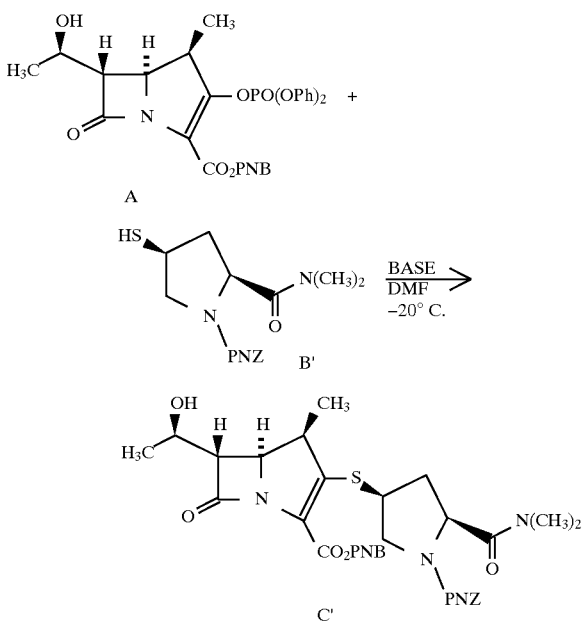

Using the procedure set forth in Example One, the base diisopropylamine was replaced with diisopropylethylamine (DIPEA).

The rate of reaction between A and B' to produce C' is significantly higher for DIPA and the other amines recited than for DIPEA.

TABLE I

| | time to 98% conversion | Assay Yield (%) | Area % purity |
|---|---|---|---|
| DBU | <0.25 h | — | — |
| DIPA | 0.5 h | 98 | 97.3 |
| TMG | 2 h | 98 | 98.0 |
| TMP | 2 h | — | — |
| DIPEA | >4 h[a] | 92[b] | — |

Reactions were conducted using equimolar amounts of A and B' at 0.1 M with 1.1 equiv of base at −20° C.
[a] about 90% conversion at 4 h.
[b] yield at 4 h.

While certain preferred embodiments have been described herein in detail, numerous alternative embodiments are contemplated as falling within the scope of the appended claims.

What is claimed is:

1. A process for synthesizing a compound of the formula I:

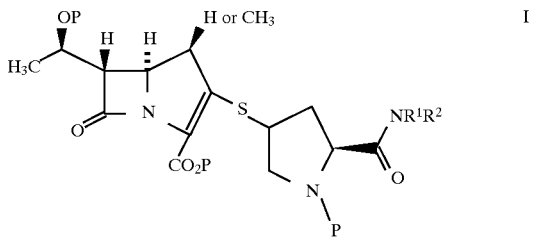

or a pharmaceutically acceptable salt or ester thereof, wherein each P independently represents H or a protecting group, and $R^1$ and $R^2$ independently represent H, $C_{1-10}$ alkyl, aryl or heteroaryl; said $C_{1-10}$ alkyl, aryl or heteroaryl being optionally substituted with one to three groups selected from the group consisting of halo, hydroxy, cyano, acyl, acylamino, aralkoxy, alkylsulfonyl, arylsulfonyl, alkylsulfonylamino, arylsulfonylamino, alkylaminocarbonyl, alkyl, alkoxy, aryl, aryloxy, amino, alkylamino, dialkylamino, carboxy and sulfonylamino, comprising:

reacting the compounds

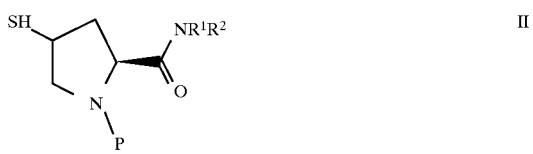

or a pharmaceutically acceptable salt, and

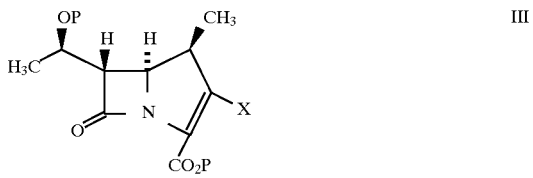

or a pharmaceutically acceptable salt or ester thereof, wherein X represents $OP(O)(OR)_2$ or $OSO_2R$, wherein R represents $C_{1-6}$ alkyl, $C_{1-6}$ alkaryl, aryl or perfluoro $C_{1-6}$ alkyl, in the presence of an amine selected from the group consisting of:

diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0.]undec-7-ene (DBU) and 1,5-diazabicyclo[4.3.0] non-5-ene (DBN).

to produce a compound of formula I.

2. A process for synthesizing a compound of the formula Ia:

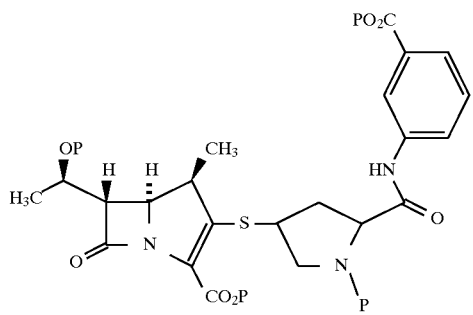

or a pharmaceutically acceptable salt or ester thereof, wherein each P independently represents H or a protecting group, comprising:

reacting the compounds:

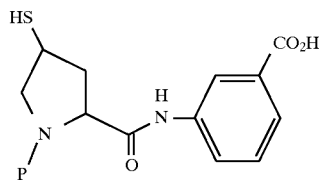

or a pharmaceutically acceptable salt or ester thereof, and

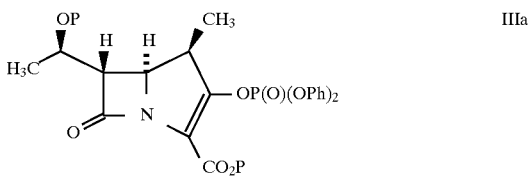

or a pharmaceutically acceptable salt or ester thereof, wherein Ph represents phenyl, in the presence of an amine selected from the group consisting of:

diisopropylamine (DIPA), dicyclohexylamine (DCHA), 2,2,6,6-tetramethylpiperidine (TMP), 1,1,3,3-tetramethylguanidine (TMG), 1,8-diazabicyclo[4.3.0]undec-7-ene (DBU) and 1,5-diazabicyclo [4.3.0]non-5-ene (DBN)

to produce a compound of formula Ia.

3. A process in accordance with claim 1 wherein the secondary amine is selected from the group consisting of: diisopropylamine (DIPA) and dicyclohexylamine (DCHA).

4. A process in accordance with claim 3 wherein the synthesis is run in a polar aprotic solvent.

5. A process in accordance with claim 4 wherein the polar aprotic solvent is selected from the group consisting of dimethylformamide, N-ethylpyrrolidinone and acetonitrile.

* * * * *